United States Patent [19]

Cain

[11] Patent Number: 5,334,205
[45] Date of Patent: Aug. 2, 1994

[54] SACROILIAC JOINT FIXATION GUIDE

[75] Inventor: James E. Cain, Mequon, Wis.

[73] Assignee: The United States of America as represented by the Secretary of the Air Force, Wright-Patterson Air Force Base, Ohio

[21] Appl. No.: 84,056

[22] Filed: Jun. 30, 1993

[51] Int. Cl.⁵ ............................................. A61F 5/04
[52] U.S. Cl. .......................................... 606/96; 606/86
[58] Field of Search ................. 606/53, 60, 61, 96-98, 606/86-89, 80, 102

[56] References Cited

U.S. PATENT DOCUMENTS

| | | | |
|---|---|---|---|
| 2,697,433 | 12/1954 | Zehnder | 606/96 |
| 4,569,338 | 2/1986 | Edwards | |
| 4,638,799 | 1/1987 | Moore | |
| 4,672,957 | 6/1987 | Hourahane | |
| 4,722,331 | 2/1988 | Fox | 606/80 |
| 4,781,182 | 11/1988 | Purnell et al. | 606/96 |
| 4,883,048 | 11/1989 | Purnell et al. | |
| 4,907,577 | 3/1990 | Wu | 606/80 |
| 4,920,958 | 5/1990 | Walt et al. | 606/96 |
| 4,985,032 | 1/1991 | Goble | 606/96 |
| 5,154,720 | 10/1992 | Trott et al. | 606/96 |
| 5,163,940 | 11/1992 | Bourque | 606/96 |
| 5,242,444 | 9/1993 | MacMillan | 606/96 |

FOREIGN PATENT DOCUMENTS

428452 5/1991 European Pat. Off. ............ 606/102

*Primary Examiner*—Ralph Lewis
*Attorney, Agent, or Firm*—Fredric L. Sinder; Thomas L. Kundert

[57] ABSTRACT

A novel guide or jig for safe and accurate placement of fixation screws across a sacroiliac joint uses the tip of a sacro-pedicle targeting screw inserted from the rear into a human sacrum as a target for guiding fixation screws. The head of the targeting screw attaches to one end of a straight first arm of a jig member. The other end of the straight arm of the jig member is attached at an angle to a semicircular second arm of the jig member. The semicircular second arm has an open slot to which is attached a bushing assembly which can be moved along and fixed in place anywhere along the slot. A cannulated pin set fits through the bushing assembly. The dimensions of the targeting screw and the jig member, including the angle between the two arms of the jig member and the radius of curvature of the semicircular second arm, are such that the cannulated pin set, when inserted through the bushing assembly, lies along a line drawn as a radius from the tip of the targeting screw. The cannulated pin set is used to guide and insert fixation screws across the sacroiliac joint. The jig insures that at any position of the bushing assembly along the semicircular second arm a fixation screw will be properly guided into position across the joint.

1 Claim, 4 Drawing Sheets

SACROILIAC JOINT FIXATION GUIDE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to surgical apparatus, and more particularly to a novel guide or jig for safe and accurate placement of fixation screws across a sacroiliac joint.

Fractures of the pelvis are potentially life-threatening. Injuries to the sacroiliac joints frequently require stabilization with screws. This has been accomplished in the past only through extensive surgical dissection and by blindly passing screws across the sacroiliac joint into the sacrum. This procedure creates a substantial risk of perforating the spinal cord, the bowel, an artery or a vein. The present invention provides a jig that safely and accurately guides fixation screws across a sacroiliac joint.

The sacrum is the large triangular bone at the base of the spine. It is made up of five vertebrae and their intervertebral discs which have fused together. The much smaller coccyx, sometimes called the tailbone, consists of three to five rudimentary vertebrae and attaches to the bottom of the sacrum to form the bottom tip of the spine. The sacroiliac joints are the mostly vertical joints where the two sides of the sacrum attach to the two ilia, or hip bones, also called pelvic bones. The ilia and their wings help form a bottom supporting structure for the internal organs and provide a pair of attachment points for the femurs or uppermost large leg bones.

The contacting surfaces of the sacrum and each ilium are covered with cartilage and fit closely together, allowing only a minimum of movement. A small synovial cavity is present between them. In later years of life, the two surfaces may actually attach. The sacrum and ilia are held together by an elaborate system of ligaments, comprising both short ligaments across the two sacroiliac joints and various longer ligaments attaching various points on the sacrum to more distant points on the ilia.

Various traumas can stretch or tear the attaching ligaments and loosen one or both of the sacroiliac joints. The most obvious result of such an injury is that movement, particularly up and down movement, can then occur along one of the joints so that a leg on that side becomes effectively shorter during walking, often about 1 inch.

When the injury to a sacroiliac joint is sufficiently severe, the joint must be repaired by fixation with surgical screws inserted across the joint. As stated earlier, this requires extensive surgical dissection. Even with extensive surgical dissection, the position of the sacrum and sacroiliac joint is difficult to accurately ascertain as a fixation screw is blindly passed through an ilium. This creates a substantial risk of perforating the spinal cord, the bowel, an artery or a vein.

It is seen, therefore, that there is a need for a guide or jig that will safely and accurately guide fixation screws across the sacroiliac joint.

It is, therefore, a principal object of the present invention to provide a safe and accurate guide for placing fixation screws across the sacroiliac joint into the sacrum.

It is a feature of the present invention that it is simple and straightforward to use.

It is an advantage of the present invention that it involves much less tissue cutting and other trauma to a patient than prior art methods.

SUMMARY OF THE INVENTION

The present invention provides a jig for safe and effective placement of fixation screws across a sacroiliac joint. The unique discovery of the present invention is that a targeting screw can be safely inserted from the rear of the sacrum, its tip precisely positioned with a fluoroscope, and its other end attached to a semicircular jig for guiding fixation screws through the sacroiliac joint along a line drawn as a radius from the tip of the targeting screw. This combination of first inserting a targeting screw through the back of the sacrum, and then using a semicircular jig to guide the fixation screws, allows the fixation screws to be inserted with minimal surgical dissection and risk of perforation of the spinal cord, the bowel, an artery or a vein.

Accordingly, the present invention is directed to a jig for guiding a fixation screw across a human sacroiliac joint, comprising a targeting screw for screwing into the rear of a sacrum, the targeting screw having a head and a tip; a jig member, including a first arm having a first end and a second end, the first end having a means for attaching the targeting screw head to the first end of the first arm and a semicircular second arm having a first end attached at an angle to the second end of the first arm, the second arm having a slot opening along its length; a bushing assembly for sliding along the slot opening of the second arm of the jig member; means for fixably attaching the bushing assembly to the second arm of the jig member at a plurality of positions along the slot opening; wherein the lengths of the targeting screw, the first and the second arms of the jig member, the angle between the first and second arms, and the radius of curvature of the semicircular second arm are such that, when the targeting screw head is attached to the first end of the first arm of the jig member, and the bushing assembly is fixed at any position along the slot opening, the axis of a cannulated pin set inserted through the bushing will lie on a radius drawn from the tip of the targeting screw.

The present invention is also directed to a method for guiding a fixation screw across a human sacroiliac joint, comprising the steps of screwing a targeting screw into the rear of the sacrum, the targeting screw having a head and a tip, attaching the head of the targeting screw to a first end of a first arm of a jig member, the jig member including a semicircular second arm attached at an angle to a second end of the first arm, the second arm having a slot opening along its length, attaching a bushing assembly to the second arm of the jig member at a first position along the slot, sliding a cannulated pin set through the bushing assembly, wherein the lengths of the targeting screw, the first and the second arms of the jig member, the angle between the first and second arms, and the radius of curvature of the semicircular second arm are such that, when the targeting screw head is attached to the first end of the first arm, and the bushing assembly is fixed at any position along the slot opening, the axis of the cannulated pin set will lie on a radius drawn from the tip of the targeting screw, and, after assembling together the targeting screw, the jig member, the bushing assembly and the cannulated pin set, using the cannulated pin set to insert a fixation screw across the sacroiliac joint.

DESCRIPTION OF THE DRAWINGS

The present invention will be more clearly understood from a reading of the following detailed description in conjunction with the accompanying drawings wherein.

DETAILED DESCRIPTION

Figure 1:
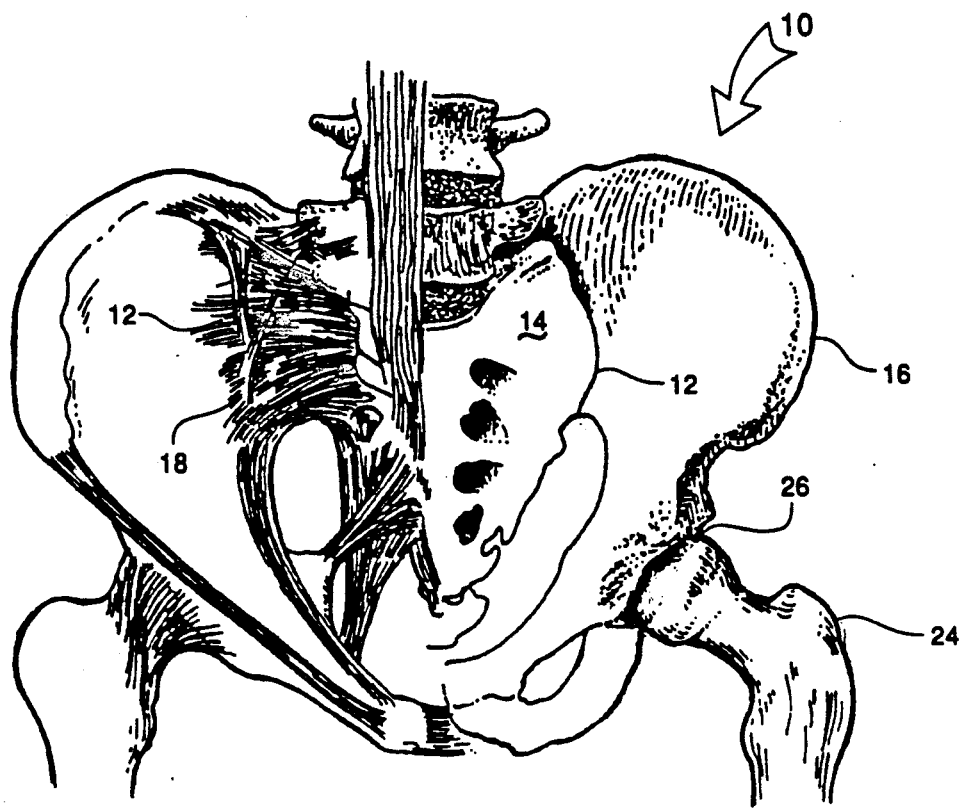
FIG. 1 is a front (or anterior) view of a male pelvis showing the sacroiliac joint connections of the sacrum to the ilia along with a few illustrative example ligaments.
Figure 2:
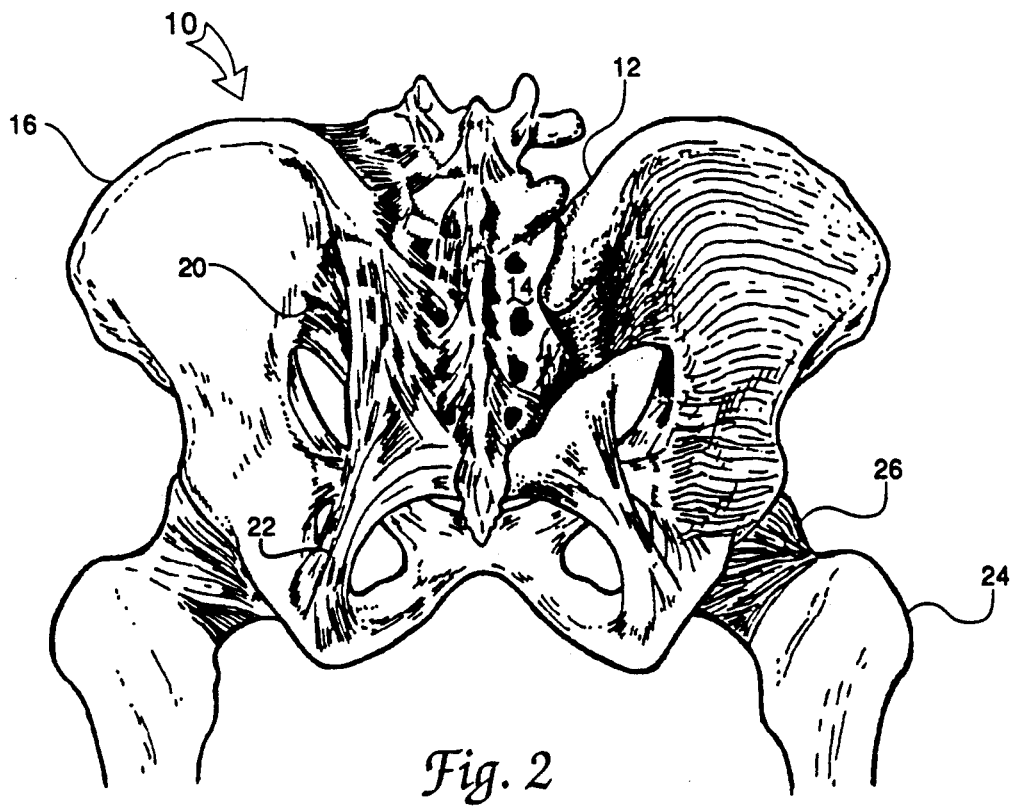
FIG. 2 is a rear (or posterior) view of a male pelvis showing the sacroiliac joint connections of the sacrum to the ilia along with a few illustrative example ligaments.

Referring now to FIGS. 1 and 2 of the drawings, there is shown, respectively, a front (or anterior) and a rear (or posterior) view of a male pelvis 10 showing the sacroiliac joint connections 12 of the sacrum 14 to the ilia 16. Also shown are a few illustrative examples, shown only on the left sides of the FIGS. 1 and 2 views, of the short ventral (front) sacroiliac ligaments 18 and dorsal (back) sacroiliac ligaments 20, and the longer sacrotuberous ligaments 22. The femurs 24 attach to the ilia 16 at hip joints 26.

FIGS. 1 and 2 illustrate the dependency of proper movement of the legs and hips on the reliability of sacroiliac joints 12. Any looseness in joints 12 will make walking both painful and difficult.

FIG. 2 also illustrates the difficulty of determining the proper direction and depth for drilling and tapping a guide hole and then screwing in a fixation screw from the dorsal side of an ilium. Even with substantial tissue dissection, the location of the sacroiliac joint is hidden from a surgeon's view. And, even if a surgeon could come in from the front, past the organs inside the abdomen, there is no clear path for inserting a fixation screw through either sacroiliac joint 12.

Figure 3:
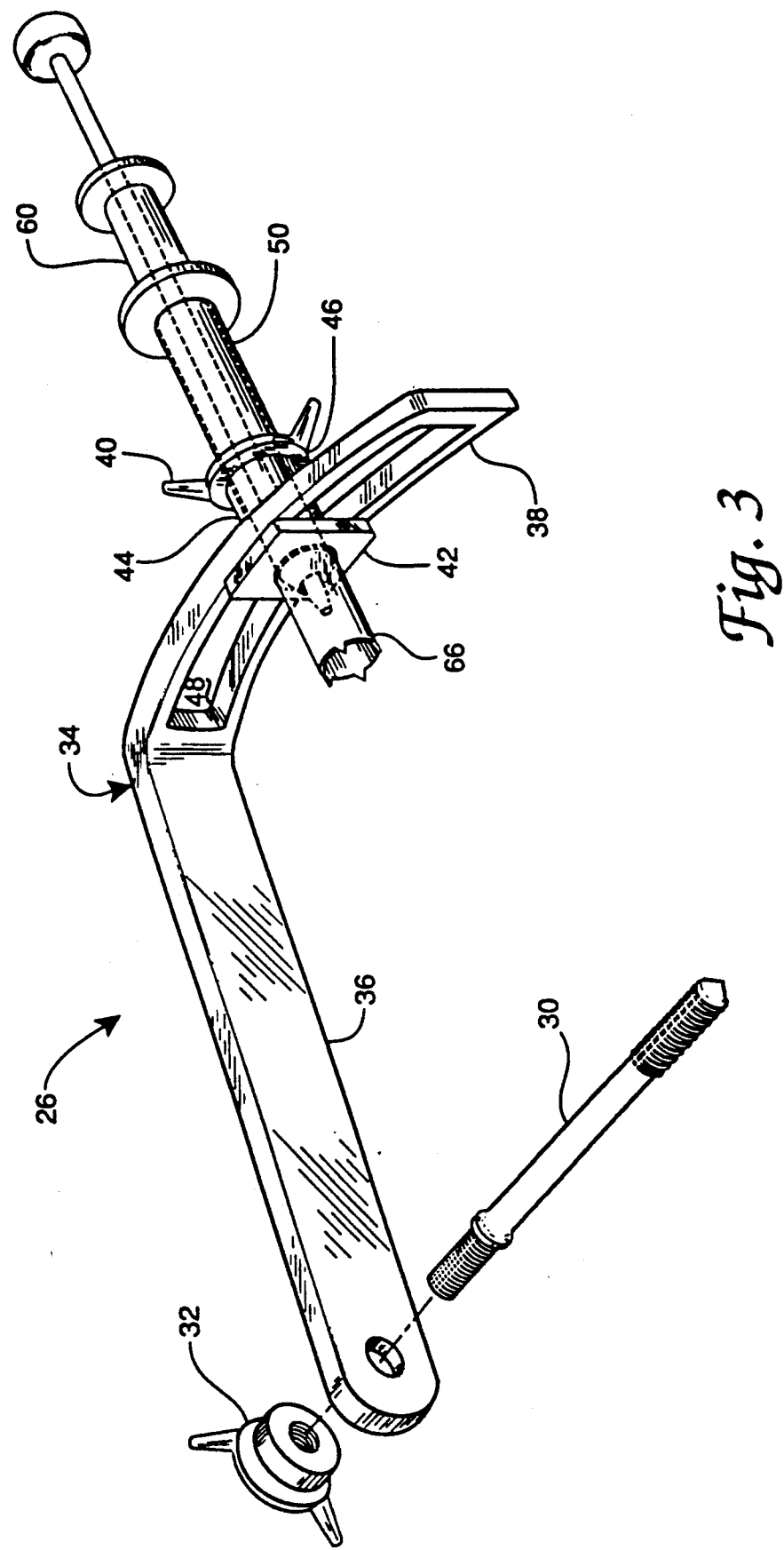
FIG. 3 is a view of a partially disassembled version of a jig built according to the teachings of the present invention.

FIG. 3 is a view of a partially disassembled version of a jig 26 built according to the teachings of the present invention. Jig 26 comprises a sacro-pedicle targeting screw 30, a wing nut 32, and a jig member 34 comprising a straight arm 36 and a slotted semicircular arm 38. A wing nut 40, opposing plate 42 and bushing 44 comprise bushing assembly 46 which can be moved along slot opening 48 and fixed in place by tightening wing nut 40. A cannulated screw (or pin) set 50 slides in and out of bushing assembly 46.

Figure 4:
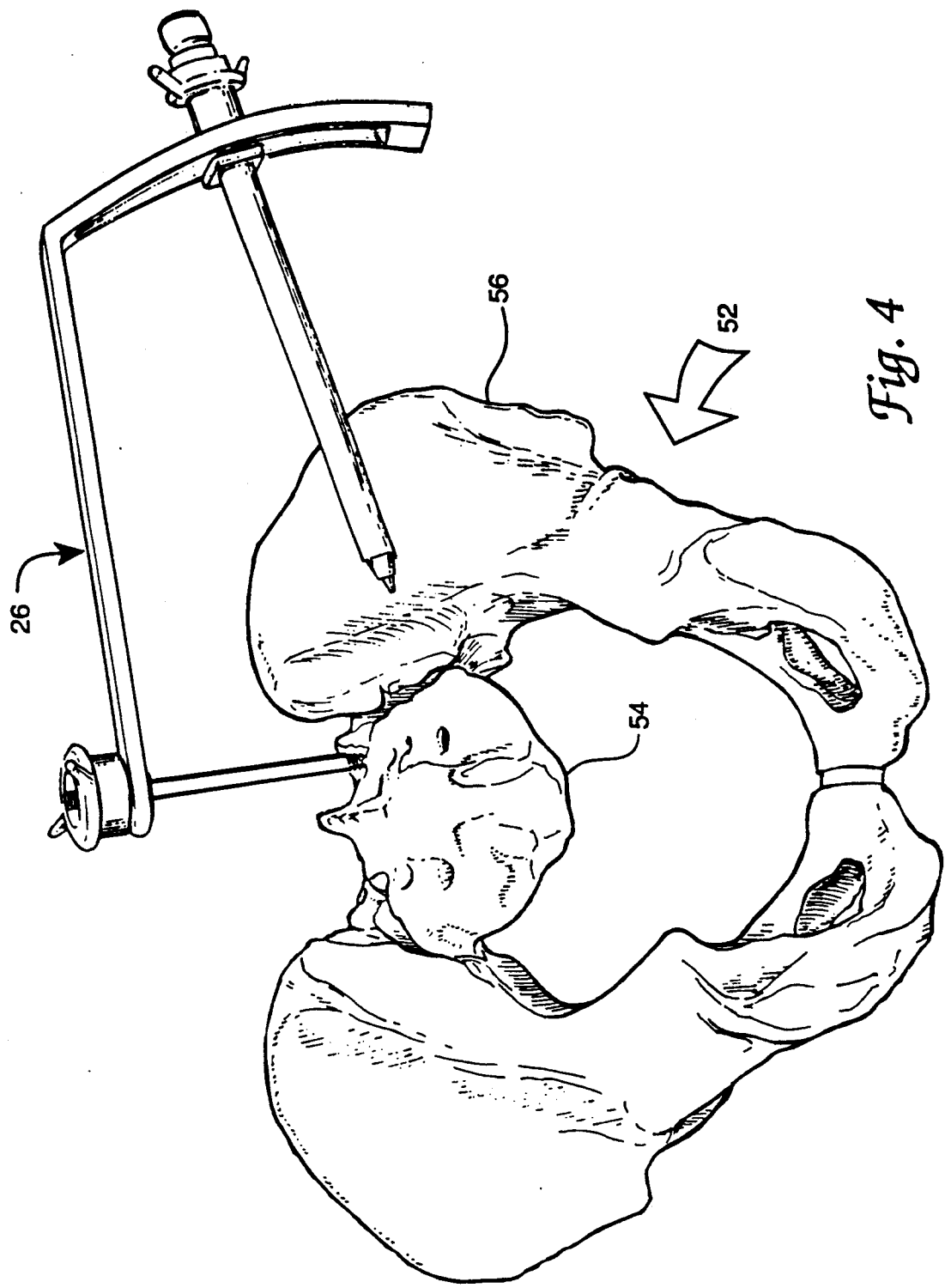
FIG. 4 is a bottom up view of a male pelvis showing the relative placement of the assembled jig of FIG. 3; and, FIG. 5 is a top down cross-sectional view of a male pelvis showing the relative placement of the FIG. 3 jig on one side of the pelvis and two already placed fixation screws through the sacroiliac joint on the other side of the pelvis.

FIG. 4 is a bottom up view of a male pelvis 52 showing the placement of jig 26 relative to sacrum 54 and ilium 56.

Figure 5:
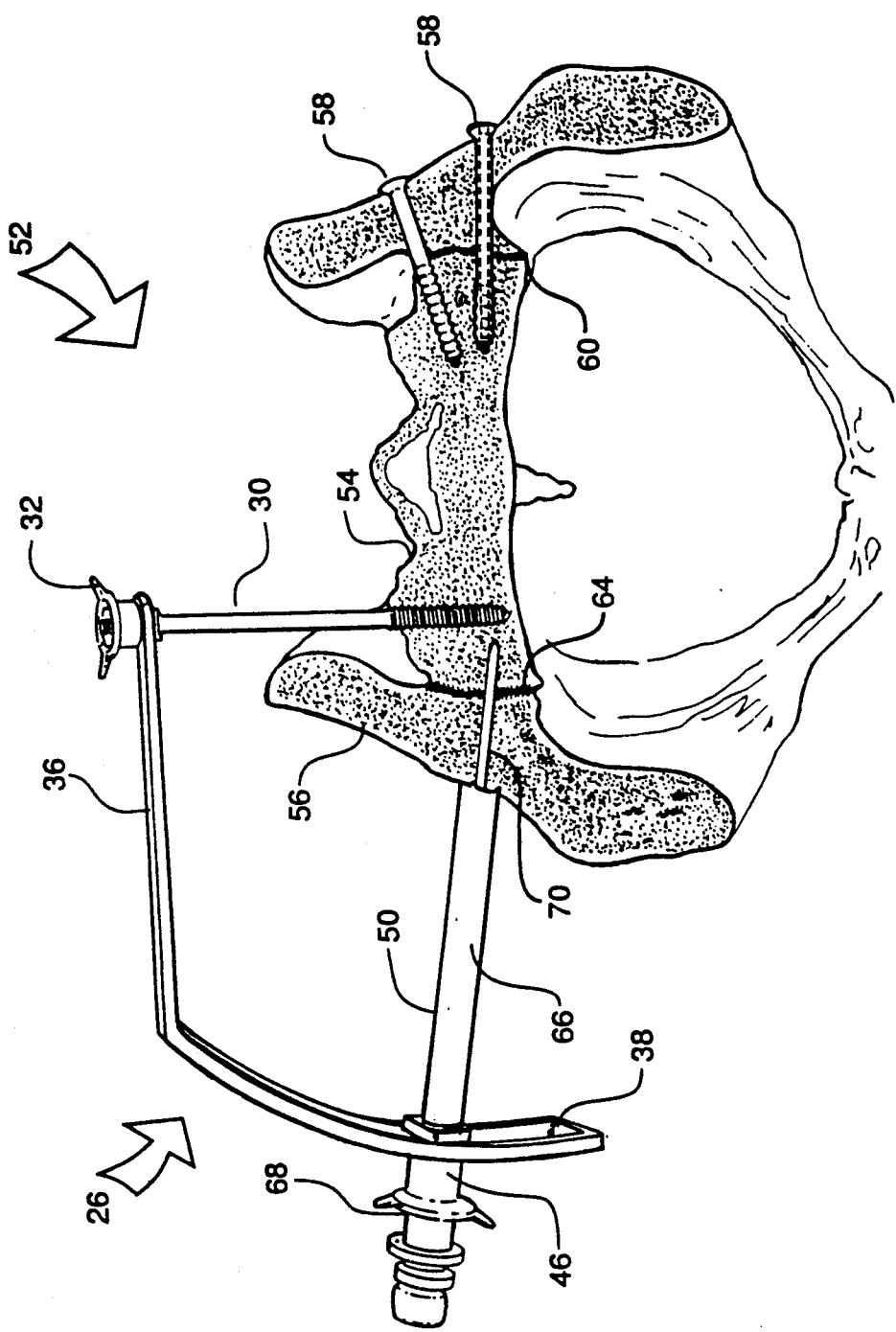

FIG. 5 is a top down cross-sectional view of pelvis 52 showing the relative positioning of jig 26 on one side of pelvis 52 and two already placed fixation screws 58 through the sacroiliac joint 60 on the other side of pelvis 52.

To use jig 26, a surgeon, using conventional surgical techniques, first inserts a targeting screw 30 into sacrum 54 from the rear, as shown in FIG. 5. This procedure requires little dissection and a much reduced risk of undesirably perforating another body structure compared to attempting to blindly insert a fixation screw directly across sacroiliac joint 64. After insertion, the patient is fluoroscoped to determine the exact position of the tip of targeting screw 30 and, if necessary, to determine any needed repositioning of the tip.

After targeting screw 30 is positioned, jig member 26 is attached to targeting screw 30 with wing nut 32 and rotated to be positioned over the dorsal side of ilium 56. Cannulated screw set 50 is then inserted through bushing assembly 46, which is fixed in place along slot opening 48 by tightening wing nut 40, and, using conventional surgical techniques, passed though the overlaying tissue until the outer cannula, or trocar, 66 presses against ilium 56 as shown in FIG. 5.

Targeting screw 30 and straight arm 36 are sized and semicircular arm 38 sized and shaped so that cannulated screw set 50 is always held by bushing assembly 46 in alignment with a radius centered at the tip of targeting screw 30. Once the tip of targeting screw 30 is properly positioned, the surgeon can use cannulated screw set 50 with jig 26 to insert any number of fixation screws 58 with both accuracy and safety. Already placed fixation screws 58 illustrate the positioning of fixation screws along radii centered at the tip of a targeting screw.

Cannulated screw, or pin, set 50 can be any of a variety of commonly available cannulated pin sets, modified as needed to fit with bushing assembly 46. In typical use, an outer cannula, or trocar, 66 is first inserted and fixed against a body structure to form an opening into the body through which the surgeon can operate. An intermediate cannula 68 is then inserted, followed by any of various inner pins 70 which may be used to drill and tap a screw hole across sacroiliac joint 64. Hollow fixation screws 58 are screwed in place across sacroiliac joint 64 by removing intermediate cannula 68 and sliding the fixation screw along inner pin 70 until screwed into the previously drilled and tapped hole. After the desired number of fixation screws 58 are in place, cannulated screw set 50 and targeting screw 30 are removed and the openings closed.

The disclosed sacroiliac joint fixation guide successfully demonstrates the use of a targeting screw inserted into a body part along a path where its position can be carefully monitored and controlled, then attaching a jig member to the back of the targeting screw and using the jig to precisely guide surgical equipment, in this case a cannulated pin set followed by fixation screws, to a location determined by the position of the targeting screw which location is otherwise generally inaccessible to precise placement by surgical equipment. Though the disclosed use is specialized, it will find application in other areas of surgery and similar mechanical tasks where accurate placement of various apparatus is difficult to accomplish directly.

It is understood that certain modifications to the invention as described may be made, as might occur to one with skill in the field of the invention, within the intended scope of the claims. Therefore, all embodiments contemplated have not been shown in complete detail. Other embodiments may be developed without departing from the spirit of the invention or from the scope of the claims.

I claim:

1. A method for guiding a fixation screw across a human sacroiliac joint, comprising the steps of:
   (a) screwing a targeting screw into the rear of the sacrum, the targeting screw having a head and a tip;
   (b) attaching the head of the targeting screw to a first end of a first arm of a jig member, the jig member including a semicircular second arm attached at an angle to a second end of the first arm, the second arm having a slot opening along its length;
   (c) attaching a bushing assembly to the second arm of the jig member at a first position along the slot;
   (d) sliding a cannulated pin set through the bushing assembly, wherein the lengths of the targeting screw, the first and the second arms of the jig member, the angle between the first and second arms, and the radius of curvature of the semicircular second arm are such that, when the targeting screw head is attached to the first end of the first arm, and the bushing assembly is fixed at any position along the slot opening, the axis of the cannulated pin set will lie on a radius drawn from the tip of the targeting screw; and,
   (e) after assembling together the targeting screw, the jig member, the bushing assembly and the cannulated pin set, using the cannulated pin set to insert a fixation screw across the sacroiliac joint.

* * * * *